(12) United States Patent
Chang et al.

(10) Patent No.: US 7,762,666 B2
(45) Date of Patent: Jul. 27, 2010

(54) DEVICE FOR MEASURING AND CORRECTING ABERRATION OF AN EYE

(75) Inventors: Chuan-Chung Chang, Hsinchu Hsien (TW); Cheng-Jong Chang, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 12/237,466

(22) Filed: Sep. 25, 2008

(65) Prior Publication Data

US 2009/0021696 A1 Jan. 22, 2009

Related U.S. Application Data

(62) Division of application No. 11/451,489, filed on Jun. 13, 2006.

(30) Foreign Application Priority Data

Nov. 16, 2005 (TW) .............................. 94140210 A

(51) Int. Cl.
*A61B 3/10* (2006.01)

(52) U.S. Cl. ...................................... 351/210; 351/205

(58) Field of Classification Search ................. 351/205, 351/210

See application file for complete search history.

(56) References Cited

U.S. PATENT DOCUMENTS

| 5,777,719 | A | 7/1998 | Williams et al. | |
| 6,582,079 | B2 | 6/2003 | Levine | |
| 2001/0041884 | A1* | 11/2001 | Frey et al. | 606/5 |
| 2002/0007176 | A1* | 1/2002 | Campin et al. | 606/5 |
| 2005/0099600 | A1* | 5/2005 | Frey et al. | 351/205 |

* cited by examiner

*Primary Examiner*—Joseph Martinez
*Assistant Examiner*—James R Greece
(74) *Attorney, Agent, or Firm*—Rabin & Berdo, P.C.

(57) ABSTRACT

A device and method for measuring and correcting eye aberrations integrate wavefront sensing, wavefront aberration correction and optometric testing into one another and configure the optical paths of wavefront sensing and optometric testing as aplanatic structures, such that under optometric testing conditions both wavefront sensing and aberration correction can be performed simultaneously, and final optometric testing is conducted on wavefront aberration-corrected optometric parameters to verify if the wavefront aberration-corrected optometric parameters fall within normal visual range, thus ensuring the accuracy and high repetition of the measured optometric parameters.

13 Claims, 2 Drawing Sheets

DEVICE FOR MEASURING AND CORRECTING ABERRATION OF AN EYE

CROSS-REFERENCE TO RELATED APPLICATION

This is a division of U.S. application Ser. No. 11/451,489, filed Jun. 13, 2006, which claimed Priority from Taiwanese application No. 094140210, filed Nov. 16, 2005, the entire disclosure of which is incorporated herein by reference.

FIELD OF THE INVENTION

The present invention is related to a method and device for measuring and correcting aberrations of an eye, more specifically, a method and device for measuring and correcting aberrations of an eye before/during/after laser ophthalmic surgery.

BACKGROUND

Wavefront technique developed by the National Aeronautics and Space Administration (NASA) was initially applied in the field of space technology. Astronomers use wavefront analysis to process aberrations produced by the atmosphere in order to obtain relatively accurate data and images of the Galaxy. At present, this epochal technique is applied in the field of human vision measurement. Light entering the eye has to pass through several structures before arriving eventually at the retina to form visual images. However, refractive index and structure of the eye varies. Shapes of these structures also affect the propagation path of light entering the eye. Due to these and other factors, the so-called "high-order aberrations" occur.

Where parallel light enters a normal eye with perfect diopter behavior, reflective light and incident light reflected from the retina of the eye are parallel light and thus sharp images are formed. Upon entry of parallel light into the eye with aberrations, the wavefront of the light reflected from the retina may be distorted due to irregular structures of the eye, causing images to be blurred, scattered, dragged and etc. Where an eye examination is conducted with a wavefront high-order aberrometer, the wavefront high-order aberrometer uses wavefront data of the light reflected from the retina to calculate variations between optical paths, calculate the average inconsistency or errors of the optical paths up to the retina, describes the degree of diffusion of a light spot, precisely carry out detection and measurement of the cornea, lens, vitreous body, retina, and others, perform integrated analysis and measurement of various factors affecting the diopter of the eye, illustrate the status of the eye with a three-dimensional drawing, and precisely measure individual parts of the cornea. The related art is disclosed in U.S. Pat. Nos. 5,777,719 and 6,582,079.

An eye wavefront measuring device disclosed in the U.S. Pat. No. 5,777,719 corrects aberrations, using an adaptive optical element, such as a deformable mirror. Elements of this kind, designed mostly in the past to correct aberrations of astronomical telescopes, are characterized by considerable aberration correction and high response speed. However, such elements do have their own disadvantages, namely bulky and expensive, thus failing to meet the need for miniaturization and popularity of the eye aberration measuring devices.

In an attempt to solve the problems of the above patent, U.S. Pat. No. 6,582,079 suggests that an adaptive element for correcting aberrations can be replaced with a micro-machined reflector or a liquid crystal phase-compensating element. The overall size and price of the proposed device can be reduced because of the element. However, this kind of wavefront measuring device does not optimize measurement and correction, resulting in great uncertainty of aberration measurement. In addition, a target object seen by an eye undergoing measurement and the optical path of the measuring device are independent of each other, and thus the difference of optometric parameters before and after aberration correction cannot be accurately determined.

Laser surgeries nowadays, whether it is Laser in Situ Keratomileusis (LASIK) or Nidek Advanced Vision Excimer Laser System (NAVEX), employ not only simple eyeglasses-fitting or correcting techniques but also several kinds of high-order instruments to measure data related to eyesight problem, such as 3-D eye auto-tracing system, iris positioning system, flying spot scanning and wavefront high-order aberration analyzers. Among them, the wavefront high-order aberration analyzer is most important to correction of eyesight, because surgery is performed with a laser-cutting instrument based on data collected from the wavefront high-order aberration analyzer. Accordingly, the accuracy of measurement is very important.

Normally, lower-order aberrations and higher-order aberrations account for approximately 85% and 15% of the refractive errors of a bad eye respectively. According to Frits Zernike, a Dutch mathematician, aberrations are classified and divided into twenty Zernike orders. The lower orders, which include the first order and second order, are related to well-known eyesight problems of myopia, astigmatism and focus. Those higher than the third order are collectively called higher-order aberrations, including coma, spherical aberration and trefoil, etc. Traditional laser-based myopic surgery only reduces lower-order aberrations by 85%. However, for a person with higher-order aberrations, even if s/he regains a visual acuity of 1.0 to 1.2 after the laser surgery, the remaining 15% higher-order aberrations will remain unsolved, and thus s/he may still experience pro-operational sequelae, such as halo, glare, dazzle, and diplopia.

Wavefront aberration analysis is presently designed to evaluate eyesight only and has disadvantages, such as low repetition of measurement and inconsistent measurement results between different brands of instruments; in consequence ophthalmic surgeons resort to clinic experience instead of instrument-generated data, thus increasing the risks of surgery. Furthermore, pre-operational and post-operational visional changes cannot be assessed by means of wavefront measuring devices nowadays, thus increasing the uncertainty of the aforesaid surgery.

Accordingly, there is an urgent need to provide a measuring method and the device thereof for solving the drawbacks of the prior art, reducing the risks of wavefront laser scanning refractive surgery, and performing eye aberration measurement and correction precisely.

SUMMARY OF THE INVENTION

In the light of the forgoing drawbacks of the prior art, an objective of the present invention is to provide an eye aberration measuring and correcting device and a method thereof so as to obtain high-repetition wavefront measurement results.

Another objective of the present invention is to provide an eye aberration measuring and correcting device and a method thereof such that optometric testing and wavefront testing are configured as aplanatic structures to enhance the accuracy of the optometric testing.

Yet another objective of the present invention is to provide an eye aberration measuring and correcting device and a method thereof so as to simplify design and fabrication.

In order to achieve the above and other objectives, the present invention provides a device for measuring and correcting eye aberrations and for use with an ophthalmic apparatus for measuring and correcting optometric parameters. The device includes: a laser unit for providing parallel light for a retina of an eye; a wavefront sensing unit for receiving and processing the light reflected by the retina, so as to generate wavefront data of wavefront aberrations based on a shift of the light; an aberration correcting unit for correcting a difference between the generated wavefront data based on the generated wavefront data; an optometric testing unit for testing and verifying wavefront aberration-corrected optometric parameters of the eye; and a beam-splitting unit disposed between the laser unit, the wavefront sensing unit, the aberration correcting unit, and the optometric testing unit for providing optical paths and optical path structures configured in such a way that the wavefront sensing unit and the optometric testing unit form aplanatic structures.

As regards the aforementioned device, the laser unit may include a laser transmitter, an attenuator and a beam expander. In another embodiment, the laser unit may further include an on-and-off controller for controlling the laser unit so as to allow the laser unit to switch properly between an on state and an off state, thus reducing the time for which the eye is irradiated by laser. The wavefront sensing unit may include a wavefront sensor and a beam expander. The wavefront sensor may include an array of microlenses and an image sensor.

The aberration correcting unit can be one selected from the group consisting of a trial lens, a liquid crystal phase modulator, a liquid zooming lens, a deformable mirror and a mirror set with a micro-brake. The optometric testing unit may include a target and a backlight module for providing light for the target. Preferably, the target is at least six meters away from the eye in order to form an image, and that the target provides the eye with at least one degree of visual angle. Furthermore, the optometric testing unit is configured to perform optometric parameter testing on at least one selected from the group consisting of visibility, degree of astigmatism and contrast.

Additionally, the aforementioned device for measuring and correcting eye aberrations of the present invention may further include a data processing unit. Preferably, the data processing unit calculates, compares and stores wavefront data of wavefront aberrations such that the stored aberration-related wavefront data become reference data for future laser ophthalmic surgery.

In order to achieve the above and other objectives, the present invention further provides a method for measuring and correcting eye aberrations and for use with an ophthalmic apparatus for measuring and correcting optometric parameters. The method comprises the steps of: testing the optometric parameters of an eye (step S1); performing wavefront measurement on the eye, so as to generate aberration-related wavefront data (step S2); correcting a difference between the generated wavefront data based on the generated wavefront data (step S3); and re-testing wavefront aberration-corrected optometric parameters of the eye to verify if the wavefront aberration-corrected optometric parameters of the eye fall within normal visual range, and in the event of any of the wavefront aberration-corrected optometric parameters outside normal visual range, the steps S2 to S4 will be repeated unless and until the wavefront aberration-corrected optometric parameters fall within normal visual range (step S4).

In the aforementioned method, the testing in the steps S1 and S4 can be performed by means of an optometric testing unit, wherein the optometric testing unit includes a target and a backlight module for providing light for the target. Moreover, the measurement in the step S2 can be performed, using a laser unit in conjunction with a wavefront sensing unit, wherein the wavefront sensing unit includes a wavefront sensor and a beam expander. The wavefront sensor further includes an array of microlenses and an image sensor. In a preferred embodiment, the laser unit includes a laser transmitter, an attenuator and a beam expander. Preferably, the laser unit further includes an on-and-off controller.

The step S3 of correcting wavefront aberrations can be performed by means of an aberration correcting unit. Preferably, the aberration correcting unit is one selected from a trial lens, a liquid crystal phase modulator, a liquid zooming lens, a deformable mirror and a mirror set with a micro-brake.

In addition, the method for measuring and correcting eye aberrations of the present invention may repeat the steps S2 and S3 unless and until a difference between the wavefront data is less than a predetermined value. Afterward, the step S4 is performed.

The device and method for measuring and correcting eye aberrations of the present invention allow wavefront sensing, wavefront aberration correction, and optometric testing to be integrated with each other, and allow the optical paths of wavefront sensing and optometric testing to be configured as aplanatic structures, such that under optometric testing conditions both wavefront sensing and aberration correction can be performed simultaneously, and final optometric testing can be conducted on wavefront aberration-corrected optometric parameters to verify if the wavefront aberration-corrected optometric parameters fall within normal visual range, thus ensuring the accuracy and high repetition of the measured optometric parameters, which provides accurate reference data for laser ophthalmic surgery, and design and fabrication of the device can be simplified. Therefore, the present invention solves the various shortcomings of the prior art.

BRIEF DESCRIPTION OF THE DRAWINGS

The present invention can be more fully understood by reading the following detailed description of the preferred embodiments, with reference made to the accompanying drawings, wherein.

DETAILED DESCRIPTION OF THE EMBODIMENTS

The present invention is described by the following specific embodiments. Those with ordinary skills in the art can readily understand the other advantages and functions of the present invention after reading the disclosure of this specification. The present invention can also be implemented with different embodiments. Various details described in this specification can be modified based on different viewpoints and applications without departing from the scope of the present invention.

It should be noted that the accompanying drawings are simplified in order to illustrate the basic structure of the present invention. Thus, only those elements related to the present invention are shown in the diagrams. The shown elements may not be drawn according to actual quantity, shape and size, which are only a matter of design choices. The layout of the elements may be more complicated than that shown.

Figure 1:
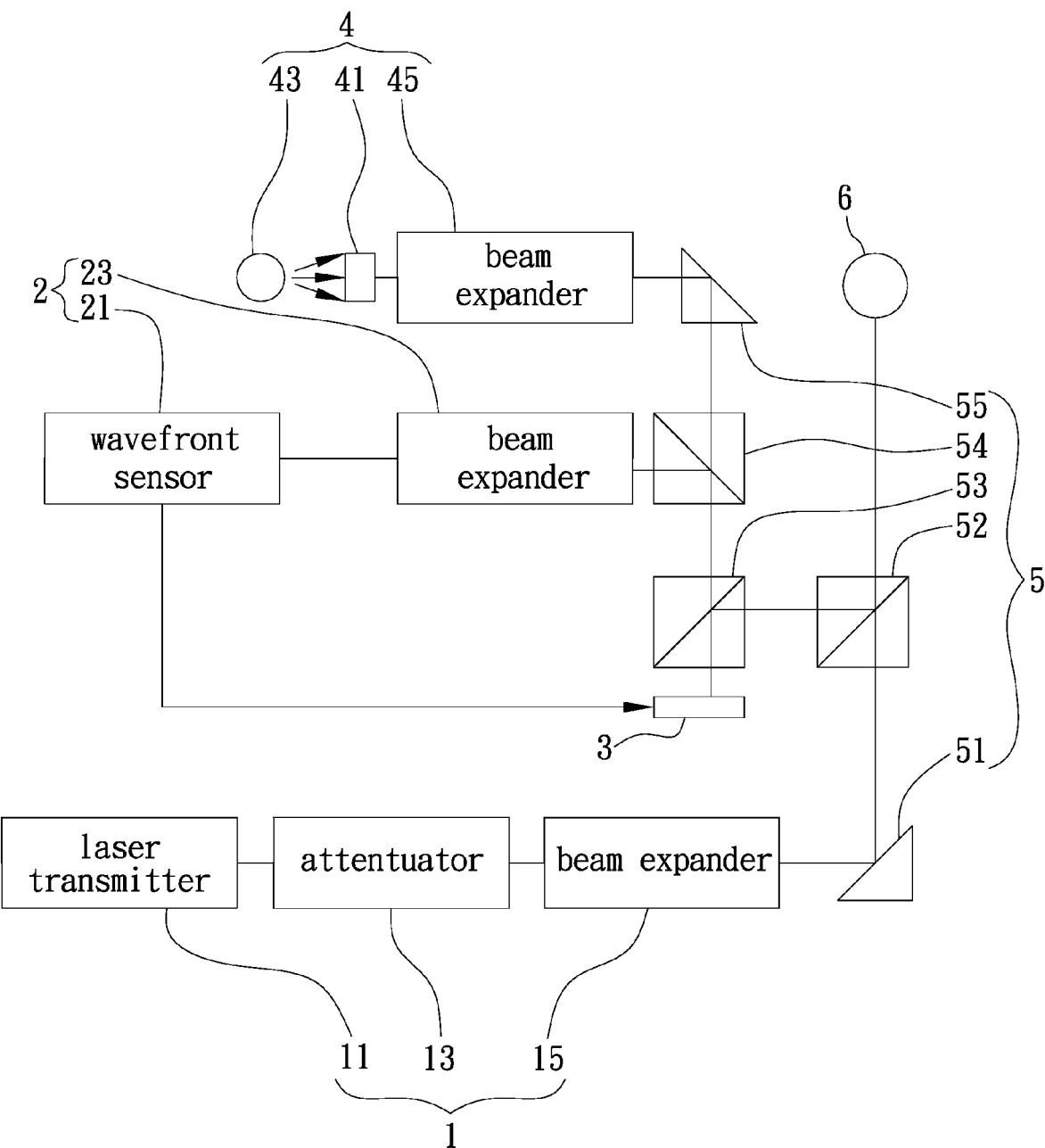
FIG. 1 is a schematic block diagram of the device for measuring and correcting eye aberrations of the present invention.

FIG. 1 is a block diagram showing an eye aberration measuring and correcting device of the present invention for use with an ophthalmic apparatus for measuring and correcting optometric parameters. The eye aberration measuring and correcting device comprises a laser unit 1, a wavefront sensing unit 2, an aberration correcting unit 3, an optometric testing unit 4, and a beam-splitting unit 5. The laser unit 1 provides parallel light for a retina of an eye. The wavefront sensing unit 2 receives and processes the light reflected from the retina so as to generate aberration-related wavefront data based on a shift of the light. The aberration correcting unit 3 corrects a difference between the generated wavefront data based on the generated wavefront data. The optometric testing unit 4 tests and verifies the wavefront aberration corrected-optometric parameters. The beam-splitting unit 5 is disposed between the laser unit 1, the wavefront sensing unit 2, the aberration correcting unit 3, and the optometric testing unit 4 and is configured to provide optical path structures, allowing the wavefront sensing unit 2 and the optometric testing unit 4 to form aplanatic structures. The beam-splitting unit 5 comprises a plurality of beam-splitting prisms 51, 52, 53, 54 and 55 disposed in the optical path structures.

The laser unit 1 includes a laser transmitter 11, an attenuator 13 and a beam expander 15. The laser transmitter 11 transmits laser light. The attenuator 13 attenuates the laser light so as to prevent the eye 6 from being harmed by the otherwise high-intensity laser light. Upon attenuation, the laser light is then passed through the beam expander 31, such that the laser light is collimated, appropriately expanded, adjusted and turned into parallel light having a cross-section as large as a light-admitting area of an optical zone of the eye 6 of a subject. Then, the parallel light is reflected into the eye 6 via the beam-splitting prism 51. During the optometric test conducted on the subject, the light is reflected from the retina of the subject eye back to the optical path structures, such that the light passing through the beam-splitting prism 52 and the beam-splitting prism 53 is refracted to the beam-splitting prism 54 and into the wavefront sensing unit 2. In another preferred embodiment, the laser unit 1 further comprises an on-and-off controller (not shown) integrated into the attenuator 13, for example, to control and allow the laser unit 1 to switch between an on state and an off state so as to reduce the time for which the eye 6 is irradiated with laser.

The wavefront sensing unit 2 comprises a wavefront sensor 21 and a beam expander 23. The wavefront sensor 21 may comprise an array of microlenses and an image sensor (not shown), for example. The image sensor is one selected from the group consisting of a CCD sensor and a CMOS sensor, both are commonly seen. After being expanded (contracted) by the beam expander 23, the aforesaid reflected light from the eye 6 enters the wavefront sensor 21 so as to be matched by the image sensor thereof, and in consequence the aberration-related wavefront data are generated based on a shift of the light.

The aberration correcting unit 3 can be one selected from the group consisting of a trial lens, a liquid crystal phase modulator, a liquid zooming lens, a deformable mirror and a mirror set with a micro-brake. The aberration correcting unit 3 receives the wavefront data sent from the wavefront sensing unit 2, and then a rotation angle per pixel, for example, of the aberration correcting unit 3 is adjusted based on the received wavefront data, such that the shift of the incident light is corrected and thus the incident light is turned into parallel light, thereby achieving the purpose of wavefront aberration correction.

The optometric testing unit 4 comprises a target 41, a backlight module 43 for providing a light source for the target 41, and a beam expander 45 for collimating light and projecting virtual images of the target 41 to the beam-splitting unit 5, thereby forming images in the eye 6 via a plurality of beam-splitting prisms 55, 54, 53 and 52 in sequence. The optometric testing unit 4 is configured for conducting optometric parameter testing on at least one optometric parameter selected from the group consisting of visibility, degree of astigmatism and contrast, and configured for outputting the corresponding optometric parameter.

The optical path structures of the wavefront sensing unit 2 and the optometric testing unit 4 are implemented by the optical path and the optical path structures disposed by the beam-splitting unit 5. Both an optometric testing path along which light starts at the optometric testing unit 4 and finally reaches the beam-splitting prism 54 through refraction by the beam-splitting prism 55, as well as a wavefront measuring path along which light returns to the wavefront sensing unit 2 via the beam-splitting prisms 52 and 53 by refraction, are configured as aplanatic structures, so as to eliminate errors caused by non-aplanatic structures to optometric testing and enhance the accuracy of the optometric testing. Additionally, the imaging distance of the target 43 is set to be at least 6 meters from the eye 6. The target 43 may also provide the eye 6 with more than one degree of visual angle to simplify design and reduce difficulty in fabrication.

Furthermore, the above eye aberration measuring and correcting device of the present invention may further comprise a data processing unit (not shown) for calculating, comparing and storing aberration-related wavefront data so that the stored aberration-related wavefront data become reference data for dioptric correction by laser surgery, for example.

Figure 2:
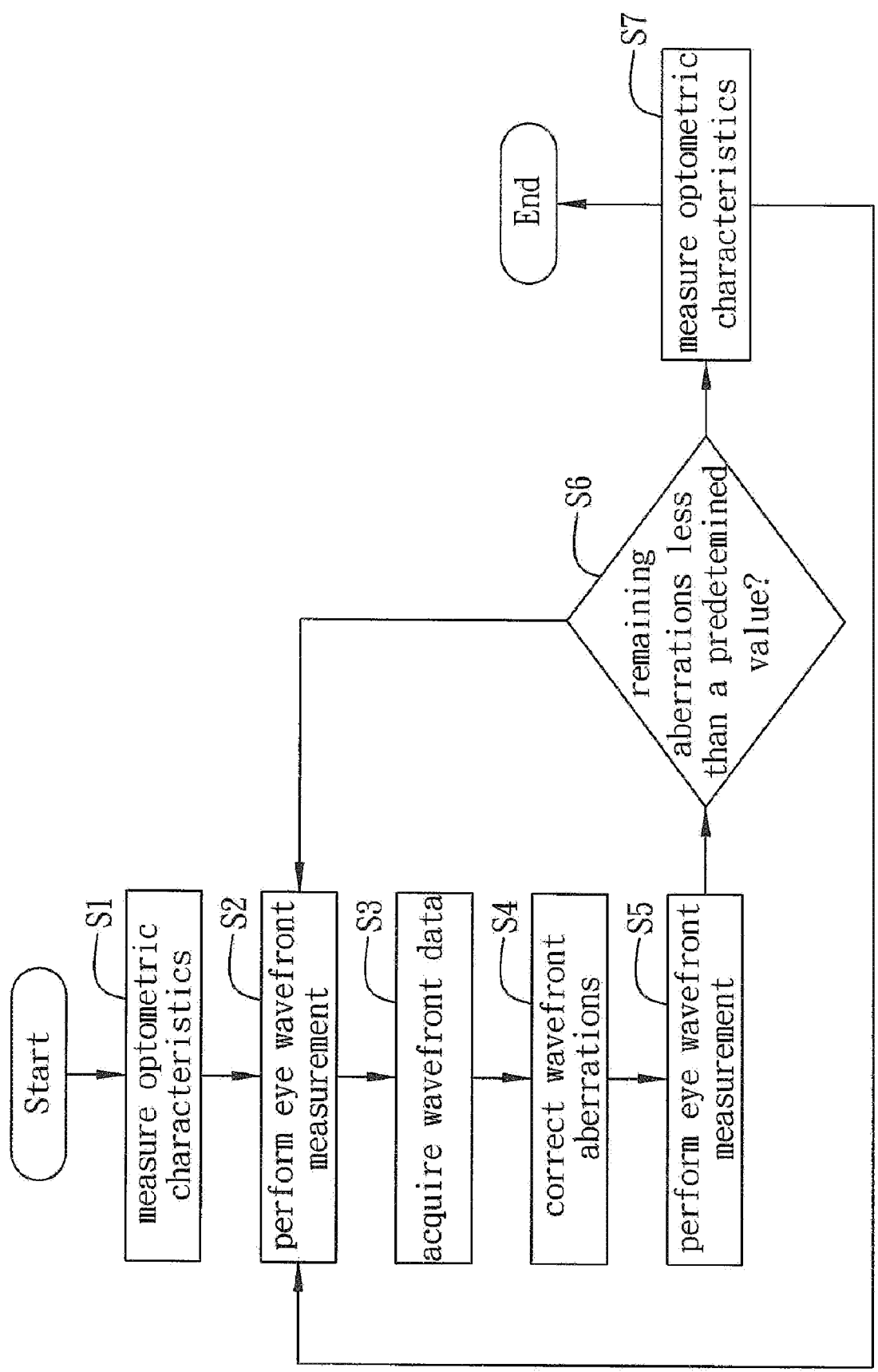
FIG. 2 is a flowchart of the method for measuring and correcting eye aberrations of the present invention.

FIG. 2 shows a flowchart of the method for measuring and correcting eye aberrations of the present invention applied to an ophthalmic instrument for measuring and correcting optometric parameters. The method for measuring and correcting aberrations of an eye includes the steps of: testing optometric parameters of an eye; performing wavefront measurement on the eye, so as to generate aberration-related wavefront data; correcting a difference between the aberration-related wavefront data based on the aberration-related wavefront data; and re-testing optometric parameters of the eye to verify if the wavefront aberration-corrected optometric parameters fall within normal visual range.

In the step S1, optometric parameters of the eye are tested. In this embodiment, the test can be performed by an optometric testing unit. The optometric testing unit may include a target, a backlight module providing light for the target, and a beam expander for collimating light and projecting virtual images of the target, such that images are formed in the subject eye through refraction by a plurality of beam-splitting prisms. Then, the step S2 is performed.

In the step S2, wavefront measurement of the eye is performed. In this embodiment, the wavefront measurement is performed, using a laser unit in conjunction with a wavefront sensing unit. The wavefront sensing unit may include a wavefront sensor and a beam expander. The wavefront sensor may comprise an array of microlenses and an image sensor. The laser unit may include a laser transmitter, an attenuator and a beam expander. The laser transmitter transmits laser light. The attenuator attenuates the laser light. Upon attenuation, the laser light is then passed through the beam expander, such that the laser light is collimated, appropriately expanded, adjusted and turned into parallel light having a cross-section as large as a light-admitting area of the optical zone of the subject eye. Then, the parallel light is reflected from a beam-splitting prism and then cast on the retina of the eye before being reflected back to optical path structures. Afterward, the parallel light is refracted by the beam-splitting prism and then enters the wavefront sensing unit. Afterward, the step S3 is performed.

In the step S3, the light reflected from the retina of the eye refracts and reaches the wavefront sensor and the image sensor thereof, for undergoing a matching process, such that the aberration-related wavefront data are generated based on a shift of the light. Then, the step S4 is performed.

In the step S4, a difference between the aberration-related wavefront data is corrected based on the aberration-related wavefront data. In this embodiment, the aberration-related wavefront data are subjected to conversion and inputted to an aberration correcting unit for correcting the difference between the aberration-related wavefront data. The aberration correcting unit may be one selected from the group consisting of a trial lens, a liquid crystal phase modulator, a liquid zooming lens, a deformable mirror and a mirror set with a micro-brake. Afterward, the step S5 is performed.

In the step S5, the wavefront measurement of the eye is performed again to acquire corrected wavefront data. The wavefront data of the aberration correcting unit are compared with that of the wavefront sensing unit again, so as to obtain the difference between the aberration-related wavefront data of the eye. Afterward, the step S6 is performed.

In the step S6, the aberration-related wavefront data difference as identified in the Step 5 is inputted into the aberration correcting unit to assess reduction of the aberration-related wavefront data difference, and then the aberration correcting unit is repeatedly adjusted by correction and comparison, so as to gradually decrease the aberration-related wavefront data difference; once the aberration-related wavefront data difference is less than a predetermined value, the step S7 will be performed; else go back to the step S2 to perform correction and comparison repeatedly.

In the step S7, optometric parameters of the eye are measured again to verify if the wavefront aberration-corrected optometric parameters fall within normal visual range. If so, then the data are stored in a data processing unit, for example, and the method ends. These data are optimized eye related wavefront data that can be used as reference data for future laser ophthalmic surgery. If the wavefront aberration-corrected optometric parameters are outside normal visual range, then the step S2 will be repeated to continue with the aforementioned correction and comparison.

Compared to the prior art, the device and method for measuring and correcting eye aberrations of the present invention allow wavefront sensing, wavefront aberration correction, and optometric testing to be integrated with each other, and allow the optical paths of wavefront sensing and optometric testing to be configured as aplanatic structures, such that under optometric testing conditions both wavefront sensing and aberration correction can be performed simultaneously, and final optometric testing can be conducted on wavefront aberration-corrected optometric parameters to verify if the wavefront aberration-corrected optometric parameters fall within normal visual range, thus ensuring the accuracy and high repetition of the measured optometric parameters, which provides accurate reference data for laser ophthalmic surgery, and the design and fabrication of device can be simplified. Therefore, the present invention solves the various shortcomings of the prior art.

The above embodiments are only illustrative of the principles of the present invention, and they should not be construed as to limit the present invention in any way. The above embodiments can be modified by those with ordinary skills in the art without departing from the scope of the present invention as defined in the following appended claims.

What is claimed is:

1. A device for measuring and correcting aberrations of an eye and for use with an ophthalmic apparatus for measuring and correcting optometric parameters, the device comprising:
    a laser unit for providing parallel light for a retina of the eye;
    a wavefront sensing unit for receiving and processing the light reflected by the retina so as to generate wavefront data of wavefront aberrations based on a shift of the light;
    an aberration correcting unit, connected only to the wavefront sensing unit, for correcting a difference between the wavefront data based on the data from the wavefront sensing unit by a physical movement so as to turn incident light into the parallel light;
    an optometric testing unit for testing and verifying the wavefront aberration-corrected optometric parameters of the eye; and
    a beam-splitting unit disposed between the laser unit, the wavefront sensing unit, the aberration correcting unit and the optometric testing unit, the beam-splitting unit being used for providing optical path structures configured in such a way that the wavefront sensing unit and the optometric testing unit form aplanatic structures.

2. The device of claim 1, wherein the laser unit includes a laser transmitter, an attenuator and a beam expander.

3. The device of claim 2, wherein the laser unit further includes an on-and-off controller.

4. The device of claim 1, wherein the wavefront sensing unit includes a wavefront sensor and a beam expander.

5. The device of claim 4, wherein the wavefront sensor includes an array of microlenses and an image sensor.

6. The device of claim 1, wherein the aberration correcting unit is one selected from the group consisting of a trial lens, a liquid crystal phase modulator, a liquid zooming lens, a deformable mirror and a mirror set with a micro-brake.

7. The device of claim 1, wherein the optometric testing unit includes a target and a backlight module for providing light for the target.

8. The device of claim 7, wherein an imaging distance of the target is at least six meters away from the eye.

9. The device of claim 7, wherein the target provides the eye with at least one degree of visual angle.

10. The device of claim 1, wherein the optometric testing unit performs optometric parameter testing on at least one optometric parameter selected from the group consisting of visibility, degree of astigmatism and contrast.

11. The device of claim 1, wherein the beam-splitting unit includes a plurality of beam-splitting prisms.

12. The device of claim 1, further including a data processing unit.

13. The device of claim 12, wherein the data processing unit calculates, compares and stores the wavefront data such that the stored wavefront data become reference data for laser ophthalmic surgery.

* * * * *